United States Patent [19]

Fauconet et al.

[11] Patent Number: 5,606,102
[45] Date of Patent: Feb. 25, 1997

[54] PROCESS FOR THE MANUFACTURE OF BUTYL ACRYLATE BY DIRECT ESTERIFICATION

[75] Inventors: Michel Fauconet, Valmont; Christian Lacroix, Folkling; Nathalie Hess; Jacqueline Bessalem, both of Saint-Avold, all of France

[73] Assignee: Elf Atochem S.A., Puteaux, France

[21] Appl. No.: 508,133

[22] Filed: Jul. 27, 1995

[30] Foreign Application Priority Data

Jul. 28, 1994 [FR] France .................................. 94 09371

[51] Int. Cl.$^6$ .................................................. C07C 69/52
[52] U.S. Cl. ............................................................ 560/205
[58] Field of Search ............................................ 560/205

[56] References Cited

U.S. PATENT DOCUMENTS

| | | |
|---|---|---|
| 3,882,167 | 5/1975 | Lohmar et al. . |
| 3,962,074 | 6/1976 | Schropp . |
| 5,093,520 | 3/1992 | Nestler et al. . |
| 5,386,052 | 1/1995 | Sakakuray et al. ................. 560/205 |

FOREIGN PATENT DOCUMENTS

| | | |
|---|---|---|
| 566047 | 10/1993 | European Pat. Off. . |
| 609127 | 1/1994 | European Pat. Off. . |
| 2186457 | 9/1976 | France . |
| 1017522 | 1/1963 | United Kingdom . |

Primary Examiner—Paul J. Killos
Attorney, Agent, or Firm—Millen, White, Zelano, & Branigan, P.C.

[57] ABSTRACT

In this esterification, catalysed by $H_2SO_4$, the crude reaction mixture comprising ester, butanol, acrylic acid, $BuSO_4H$ and traces of $H_2SO_4$ is obtained; $BuSO_4H$ is hydrolysed (in R2) to $H_2SO_4$ using pure water or water generated during the reaction; after hydrolysis, the medium is separated by settling (in D2) into an organic phase containing ester, butanol and part of the unconverted acid; and an aqueous phase containing $H_2SO_4$ and the remainder of the unconverted acid; the organic phase is washed under alkaline conditions in order to neutralize the acrylic acid to alkaline acrylate which is soluble in the aqueous phase and then the neutralized organic phase is washed with water; the acid present in alkaline salt form in the aqueous phase from the 1st basic neutralization is regenerated by addition of the acidic aqueous phase (8) resulting from the separation by settling (in D2) of the hydrolysis stage; the acid (10) thus regenerated in this aqueous phase is extracted (in C5) by a solvent chosen from butanol, butyl acrylate or a mixture of butyl acrylate and butanol; the organic phase (13) obtained at the head of the extraction column (C5), containing mainly acid and butanol or ester, or a mixture of butanol and ester, is recycled to the esterification reactor (R1); the aqueous phase (15) recovered at the foot of the column (C5) is conveyed as feed to a distillation column (C6) for recovering butanol (16) at the head, for the purpose of recycling it upstream and of discarding the spent aqueous liquors, which are virtually free from organic pollution.

11 Claims, 2 Drawing Sheets

5,606,102

PROCESS FOR THE MANUFACTURE OF BUTYL ACRYLATE BY DIRECT ESTERIFICATION

The present invention relates to a process for the manufacture of butyl acrylate by direct esterification of acrylic acid by butanol, the said esterification being catalysed by sulphuric acid, the water of reaction being removed, during all or part of the reaction, in the form of an azeotropic mixture with butanol and butyl acrylate, the crude reaction mixture obtained comprising butyl acrylate, butanol, acrylic acid, butyl hydrogen sulphate and traces of sulphuric acid.

The synthesis of acrylates by esterification of acrylic acid and, in particular, of butyl acrylate has been widely described in the literature.

The esterification reaction is an equilibrium reaction, generally catalysed by an acid. Two main catalytic routes are principally described:

homogeneous catalysis, most often in the presence of sulphuric acid or sulphonic acids, the reaction being carried out non-continuously or continuously;

heterogeneous catalysis, based on solid catalysts, generally of acid resin type, and a reaction carried out continuously.

In each of these cases, the water generated during the reaction can be removed simultaneously with its formation or separated in a second stage. The removal of this water is, in general, carried out by distillation, in the form of an azeotropic mixture with the esterifying alcohol or a solvent added before reaction.

For reasons of increase in productivity and of making it easier to carry out the reaction, it may be preferable to carry out the reaction continuously. However, this route has the disadvantage, if it is not desired to increase indefinitely the number of reaction stages, of limiting the degree of conversion of the reactants.

In particular, in the case of the manufacture of butyl acrylate, acrylic acid and the ester have very similar boiling points and it is economically very difficult to separate the two components by an ordinary distillation.

The use of a catalyst of heterogeneous type has the advantage of facilitating the separation and the recycling of the catalyst.

This type of catalyst has been extensively described, as in French Certificate of Addition No. 2,186,457, in which the water of reaction is removed as it is formed, in order to promote the conversion of the reactants. This process, which uses acid resins as catalysts, has the disadvantage of generating by-products of dialkyl ether type, in larger amounts than homogeneous catalysis by sulphuric acid. In particular, in the case of the manufacture of butyl acrylate, dibutyl ether is generated, which is difficult to separate from butyl acrylate by distillation. This ether formation is additionally favoured in this medium by the absence of water and the presence of a significant amount of butanol.

In order to reduce this disadvantage, which is related to the use of acid resin catalysts, it has been proposed, in American Patent U.S. Pat. No. 4,012,439, to carry out the reaction stage without simultaneously removing the water of reaction. This necessitates carrying out the reaction under pressure in order to keep the constituents of the mixture in the liquid state. In addition, this way of carrying out the reaction reduces the kinetics and the degree of conversion of acrylic acid, which requires carrying out the reaction at high temperatures and in the presence of a large excess of alcohol. The consequence is that the reaction medium contains high concentrations of water, butanol and acrylic acid, which promotes, under the effect of the temperature, the formation of heavy products resulting from addition reactions of water, butanol and acrylic acid to the double bonds of the acrylic acid and the butyl acrylate. The formation of these heavy impurities leads, in addition, to a reduction in the activity and in the lifetime of the catalyst by fouling the active pores of the resin.

The use of homogeneous catalysis, in particular of sulphuric acid, greatly reduces these disadvantages related to the formation of undesirable by-products but poses the problem of the separation of the catalyst after reaction, which is added to the concern to remove the residual acrylic acid, in order to avoid contamination of the pure butyl acrylate by this unconverted reactant.

Sulphuric acid is often preferred, mainly due to its activity and its low cost, which makes economically viable a removal process which does not involve recycling.

Thus, the joint removal of acrylic acid and the catalyst by an alkaline neutralization of their acidities, for example in the presence of sodium hydroxide, is described.

This technique, simply used, has significant disadvantages:

in the reaction medium, sulphuric acid reacts with butanol and is present in the form of butyl hydrogen sulphate, which is the true catalyst of the reaction. During the alkaline neutralization stage by sodium hydroxide, this compound is converted to neutral butyl sulphate, which cannot be distilled in a subsequent distillation stage of the aqueous effluents. Consequently, this compound is found in the spent aqueous liquors discharged by the factory, which causes significant organic pollution, measurable in the form of COD;

excess acrylic acid, which has not reacted during the reaction, also constitutes a significant source of organic pollution, discharged in the alkaline salt form (sodium acrylate) in the spent aqueous liquors from the factory. In addition, this removal leads to a loss in yield of acrylic acid to butyl acrylate.

In order to reduce the organic pollution caused by the discharge of neutral butyl sulphate in the spent aqueous liquors, a process is described in French Patent Application No. 93-00827 of Jan. 27, 1993, on behalf of the Applicant Company, which is targeted at hydrolysing buryl hydrogen sulphate in acidic medium, in order to convert it back to butanol and original sulphuric acid which can be removed after neutralization without increasing aqueous organic pollution. This treatment has the disadvantages of requiring a significant addition of sulphuric acid, in order to neutralize all the alkaline species present on conclusion of the neutralization stage (sodium acrylate and neutral butyl sulphate) and in order to catalyse the hydrolysis reaction, the consequence of which is a high discharge of alkaline salts after further neutralization of the acid species.

The process for separation of acrylic acid from the reaction medium from a synthesis of butyl acrylate, described in American Patent U.S. Pat. No. 4,012,439, in the case of an esterification catalysed by acid resins, is not simply applicable in the case of an esterification catalysed by sulphuric acid, because separation of the light constituents (butyl acrylate, butanol, water) from the heavy compounds (catalyst, acrylic acid, inhibitors, and the like) would require distillation under very corrosive conditions, due to the presence of the catalyst in the column and at the foot of the column, and thus recours to expensive special materials. In addition, the presence of catalyst at high concentrations in the column, in the presence of water, leads to partial hydrolysis of the butyl acrylate formed, resulting in a reduction in the yield of the synthesis.

The simultaneous recovery of acrylic acid and the catalyst is described in American Patent U.S. Pat. No. 5,093,520 in the case of a synthesis of 2-ethylhexyl acrylate, using two complementary stages:

extraction with water of the acrylic acid and the 2-ethylhexyl hydrogen sulphate present in the reaction medium;

extraction with the alcohol 2-ethylhexanol of the acrylic acid and the 2-ethylhexyl hydrogen sulphate present in the aqueous phase of the first extraction stage.

The process requires the use of a solvent, added to the reaction stage, in particular for favouring the extraction yield of the compounds in the first extraction stage. The use of a solvent requires a separation and recovery stage, which is expensive. Moreover, even under these conditions, the extraction yields are low, especially as regards acrylic acid. This process is not applicable to the synthesis of butyl acrylate, because the unextracted acrylic acid is very difficult to separate from the ester. Moreover, the extraction yield of butyl hydrogen sulphate by butanol would be lower than for the extraction of 2-ethylhexyl hydrogen sulphate by 2-ethylhexanol, due to the greater solubility of alcohol in water in the case of butanol, which has the effect of carrying a portion of the catalyst into the aqueous phase. The consequence would be the discharge of significant organic pollution in the spent aqueous liquors from the factory.

American Patent U.S. Pat. No. 3,882,167 describes a process for the synthesis of acrylic esters with heterogeneous catalysis by acid resins, in which are described:

the recovery of acrylic acid in the reaction medium in a first alkaline extraction stage;

a reacidification of the acrylic acid salt;

a second extraction stage of the acrylic acid regenerated above using a mixture of light products, mainly comprising alcohol, ester, dialkyl ether and water, recovered at the head of the topping column for the reaction medium.

This process has the disadvantage of constituting a loop of increasing concentration of light impurities, in particular ether, which finally emerges in the pure product.

In addition, as in the case of American Patent U.S. Pat. No. 5,093,520, it would not be applicable in the case of the synthesis of butyl acrylate by homogeneous catalysis, due to the imperfect extraction yield of butyl hydrogen sulphate by butanol.

American Patent U.S. Pat. No. 3,962,074 describes, in a way very analogous to American Patent U.S. Pat. No. 3,888,167 mentioned above, the separation of acrylic acid from acidic aqueous solutions by extraction using a mixture of butanol and butyl acrylate.

The application of all these processes to the recovery of acrylic acid and buryl hydrogen sulphate using butanol or mixtures of butyl acrylate and butanol moreover has the disadvantage of carrying, into the extract, a high concentration of water and dissolved salts arising from the prior neutralization of the acids. During recycling of the extract in the esterification stage, the high concentration of water in this extract increases the reaction time. Moreover, during this stage, in which the water present is removed, the dissolved salts precipitate in the reaction medium, with the risk of blocking the pipework or of wearing away the wall of the reactor.

In order to reduce these disadvantages, butyl acrylate, or a mixture of butyl acrylate and butanol which is rich in ester, could be used, which would make it possible to reduce entrainment of water and salts in the extract. Unfortunately, the extraction yield of butyl hydrogen sulphate decreases when the ester/alcohol ratio in the solvent increases.

When applied to a complete synthetic process for butyl acrylate catalysed by sulphuric acid, all these processes generate a large amount of salts and do not make it possible to solve the problem of removal of the catalyst, butyl hydrogen sulphate, which is responsible for a large part of the aqueous pollution discharged.

The main object of the present invention is to provide an improved process for the manufacture of butyl acrylate, by direct esterification without solvent, in the presence of sulphuric acid used as catalyst, this process having to make it possible to reduce, in an economical way, the organic pollution and the saline discharges in the aqueous liquors discarded, by taking care:

to separate completely the acrylic acid present in the crude mixture after reaction in order to prevent it from being entrained in the pure ester;

to recover as much as possible of this acrylic acid, for the purpose of recycling it, reducing its losses which generate organic pollution in the aqueous effluents of the process;

to reduce as much as possible the organic pollution discharged in the aqueous effluents of the process caused by the presence of butyl hydrogen sulphate in the reaction medium; and to reduce the amounts of neutralizing agents, responsible for the formation of salts, by recycling the acidic aqueous phase from the hydrolysis stage of the butyl hydrogen sulphate to the regeneration stage of acrylic acid which has been neutralized beforehand.

To this end, the process for the manufacture of butyl acrylate, as it is defined in the preamble of the present description, is, in accordance with the present invention, characterized in that:

(a) butyl hydrogen sulphate is hydrolysed to sulphuric acid using pure water and/or using water generated during the reaction;

(b) the medium, after hydrolysis, is separated by settling into:

an organic phase containing butyl acrylate, butanol and a part of the unconverted acrylic acid; and an aqueous phase containing sulphuric acid and the remainder of the unconverted acrylic acid;

(c) the organic phase is washed under alkaline conditions for the purpose of neutralizing the acrylic acid to alkaline acrylate which is soluble in the aqueous phase and the neutralized organic phase is then washed with water;

(d) the acrylic acid present in the alkaline salt form in the aqueous phase of the first basic neutralization is regenerated by addition of the acidic aqueous phase resulting from the separation by settling of the hydrolysis stage and, optionally, of a complement of sulphuric acid;

(e) the acrylic acid thus regenerated in this aqueous phase is extracted by a solvent chosen from butanol, butyl acrylate or a mixture of butyl acrylate and butanol;

(f) the organic phase obtained at the head of the extraction column, containing acrylic acid and butanol or butyl acrylate or a mixture of butanol and butyl acrylate, is recycled in the esterification reactor;

(g) the aqueous phase, recovered at the foot of the solvent extraction column, is conveyed, optionally after neutralization with sodium hydroxide, as feed to a distillation column which makes it possible to recover butanol at the head, for the purpose of recycling it upstream in the process, and to discard the spent aqueous liquors, which are virtually free from organic pollution.

The hydrolysis in stage (a) can be carried out in a stirred reactor or a plug flow reactor, to which is sent the crude reaction mixture obtained after the end of the esterification reaction, at a temperature of 50° to 200° C., preferably between 70° and 150° C., and at a pressure which is sufficient to prevent boiling of the medium, by adding pure water and/or water generated by the esterification reaction, in a proportion of 3 to 50% by weight with respect to the crude reaction mixture, preferably between 4 and 20% by weight, for a time from 10 seconds to 2 hours, preferably between 10 seconds and 1 hour.

The two washing operations of stage (c) can be carried out in a washing column supplied:

at the bottom, with the organic phase resulting from the hydrolysis stage;

in the middle of the column, with an aqueous sodium hydroxide solution;

at the head of the column, with fresh water or the remainder of the water of reaction unused in the hydrolysis stage.

In accordance with a preferred embodiment, the two washing operations of stage (c) are carried out by neutralizing the organic phase resulting from the decanter with a basic solution and by sending the resulting neutralized phase to a new decanter, the organic phase resulting from the said decanter being conveyed to the foot of a washing column supplied at the head with pure water and/or a portion of the water generated in the esterification reaction, the phase drawn off from the foot of the said washing column being sent to the above-mentioned distillation column.

Preferably, the extraction stage (e) is carried out in an extraction column supplied at the head with the acidified aqueous phase and, at the foot, with the solvent.

The said solvent can comprise all or part of the butanol necessary for the esterification reaction, optionally completed by all or part of a mixture mainly comprising butyl acrylate and butanol, resulting from columns for topping the washed crude reaction mixture and the aqueous effluents of the process. However, the said solvent can advantageously be composed of pure butyl acrylate with, if appropriate, butanol, the butyl acrylate/butanol ratio by weight being in particular between 1/0 and 1/0.5 and preferably between 1/0 and 1/0.7. According to a particularly advantageous embodiment, the solvent is composed of all or part of the washed crude reaction mixture or is composed of a mixture of pure butyl acrylate and all or part of the flows obtained at the head of the columns for topping the washed crude reaction mixture and the aqueous effluents of the process.

The process according to the present invention can be carried out continuously or non-continuously.

Figure 1:
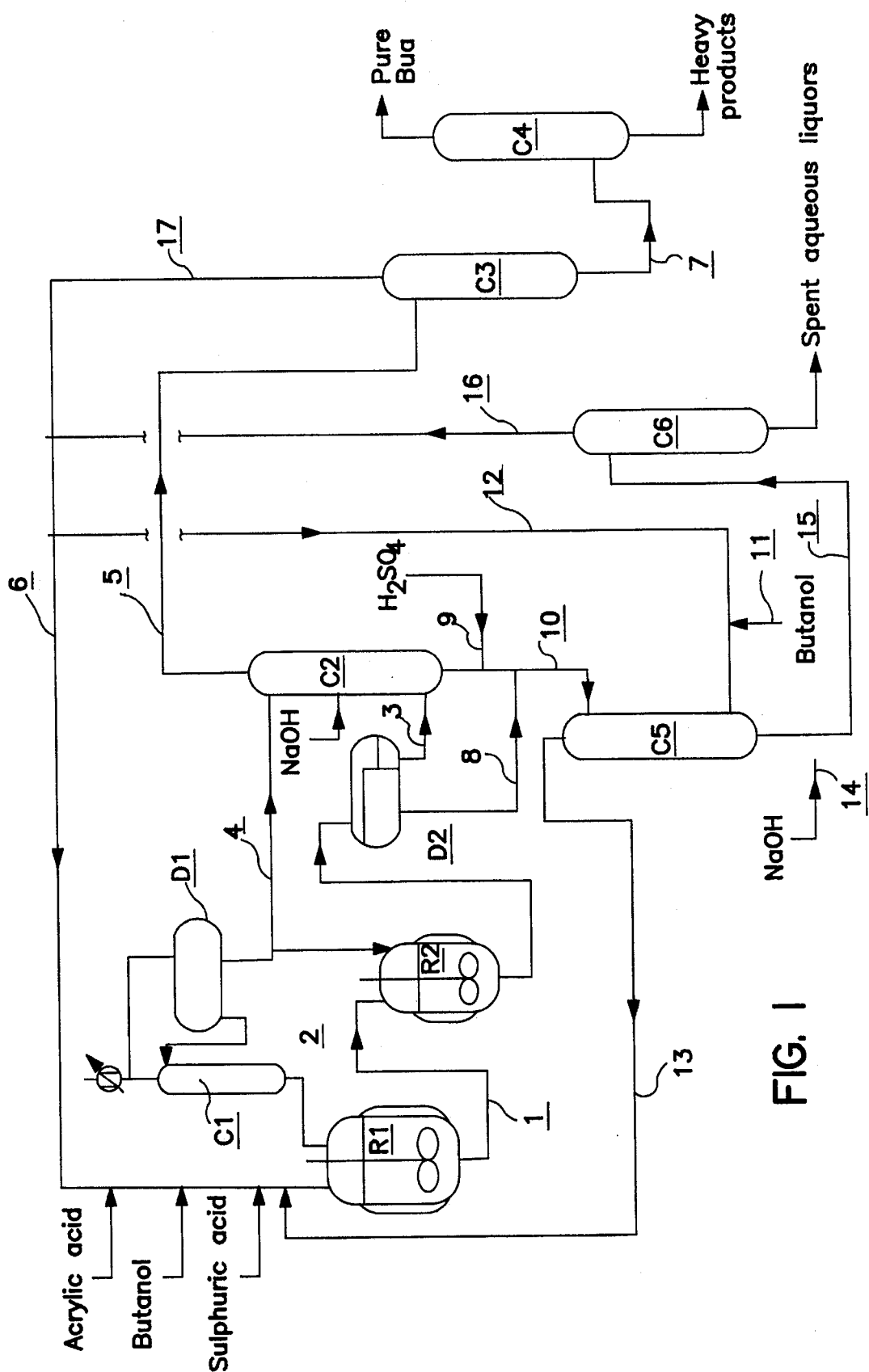
FIGS. 1 and 2 in the appended drawing each represent a scheme of the process of manufacture of butyl acrylate according to the invention.

It can be seen, in FIG. 1, that, in a first stage, which can be carried out non-continuously or continuously, a mixture comprising fresh acrylic acid, fresh butanol and sulphuric acid used as catalyst, as well as a mixture of ester and butanol (6) and a mixture of butanol, ester and acrylic acid (13), recovered downstream of the reaction in the process described, are conveyed into the reaction part, which can comprise one or a number of reactors in series R1 surmounted by one or a number of columns C1. The water generated during the reaction is distilled during the reaction, in the form of an azeotropic mixture with the alcohol and the ester, and then separated in the decanter D1, where the aqueous phase is drawn off and the organic phase is conveyed to the head of the column C1.

The reaction mixture is conveyed via the pipe 1 to a reactor R2, where hydrolysis of butyl hydrogen sulphate is carried out, with a part of the aqueous phase recovered in the decanter D1, conveyed via the pipe 2.

The two-phase medium obtained is conveyed to a decanter D2, where it is separated into an organic phase, conveyed via the pipe 3 to the foot of an extraction column C2. This column is also supplied, at the head, with the remainder of the aqueous phase recovered in the decanter D1, via the pipe 4, and, in the middle of the column, with sodium hydroxide.

The organic phase, obtained at the head of the column C2, is conveyed, via the pipe 5, to a column C3, where the light products (BUA, butanol, water) are recovered at the head (pipe 17); these light products will be recycled to the reaction stage via the pipe 6. The foot of the column C3 supplies a column C4 (flow 7), which makes it possible to separate pure ester at the head from the heavy products at the foot.

The alkaline aqueous phase, recovered at the foot of the column C2, is acidified with the acidic aqueous flow separated in the decanter D2 (pipe 8), optionally completed with sulphuric acid (pipe 9). The acidified flow is conveyed, via a pipe 10, to the head of an extraction column C5, supplied at the foot with all or part of the fresh butanol necessary for the esterification (pipe 11) and all or part of the flow 12 recovered at the head of the topping columns.

On departure from this column C5, the organic phase recovered at the head is recycled, via the pipe 13, as feed for the reaction stage and the aqueous phase obtained at the foot is conveyed, after neutralization of the acids with sodium hydroxide (in 14), to a distillation column C6 (flow 15).

This column C6 makes it possible to recover, at the head, the light organic compounds (mainly butanol) in order to recycle them upstream in the process, via the pipe 16, and to discharge, at the foot, an aqueous flow which is free from a large part of its organic pollution.

Figure 2:
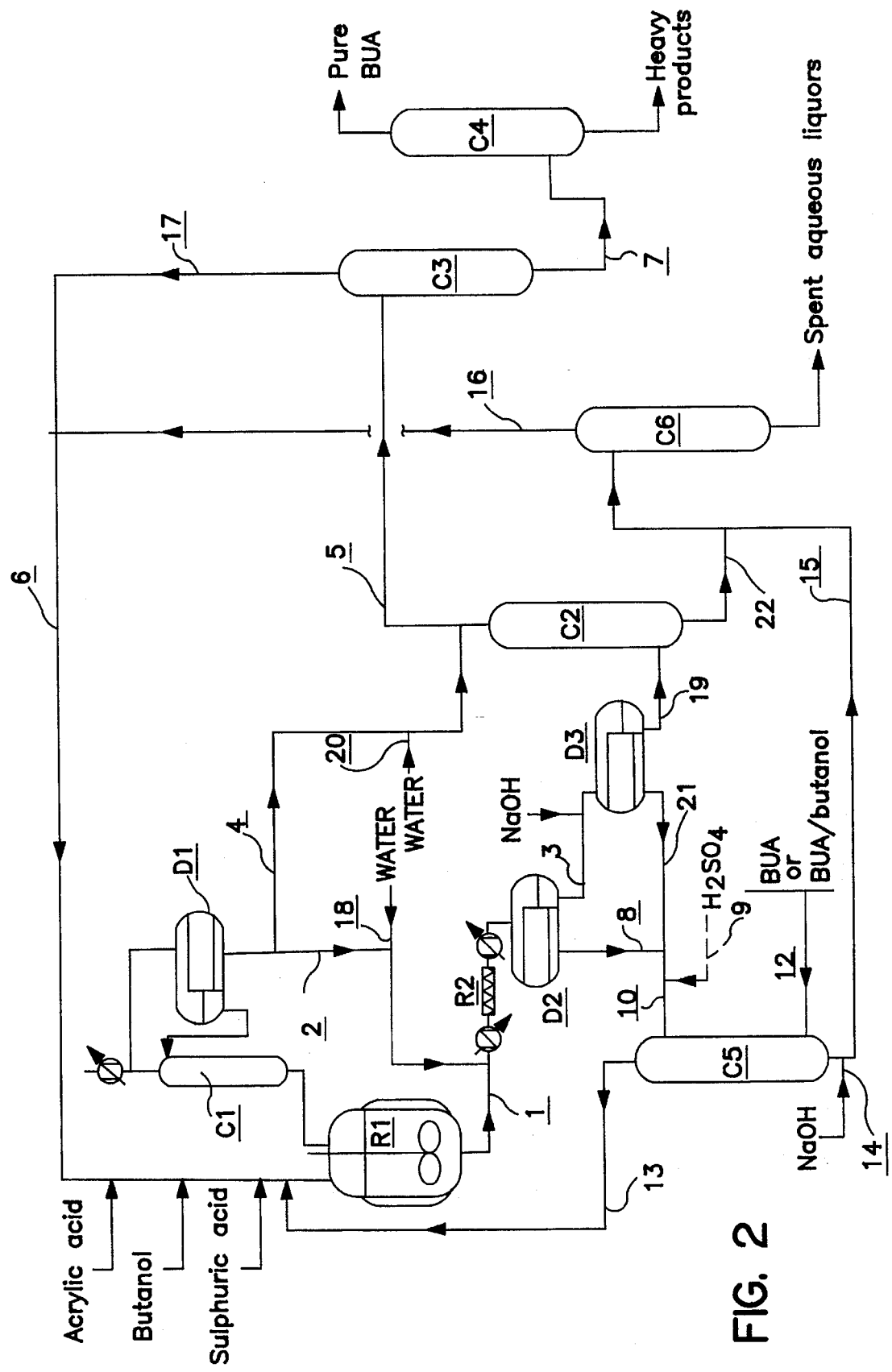

If reference is now made to FIG. 2, it can be seen that a reaction scheme for the manufacture of butyl acrylate has been represented which differs from that in FIG. 1 in the following three points:

Hydrolysis of butyl hydrogen sulphate is carried out in a plug flow reactor R2 with pure water 18 and/or a part of the aqueous phase recovered in the decanter D1, conveyed via the pipe 2.

The organic phase 3, resulting from the decanter D2, is neutralized with a basic (NaOH) solution and the two-phase medium is separated in a new decanter D3. The organic phase 19 from the decanter D3 is conveyed to the foot of a washing column C2 supplied at the head with pure water 20 and/or the remainder of the aqueous phase recovered in the decanter D1, via the pipe 4. The phase 22 drawn off at the foot of the column C2 is sent as feed to the column C6.

The alkaline aqueous phase, recovered in the decanter D3 (flow 21), is acidified with the acidic aqueous flow separated in the decanter D2 (pipe 8), optionally completed with sulphuric acid (pipe 9). The acidified flow is conveyed, via a pipe 10, to the head of an extraction column C5, supplied at the foot (pipe 12) with pure butyl acrylate or a mixture of butyl acrylate and butanol, composed for example of a part of the flow 5 obtained at the head of column C2 or composed of a mixture of pure butyl acrylate and all or part of the flows 16 and/or 17 obtained at the head of the columns C6 and C3.

In order to illustrate further the subject of the present invention, a description thereof will be given below, with reference to FIG. 1, of an implementational example (Example 1) and of a comparative example (Example 2) and, with reference to FIG. 2, of an implementational example (Example 3), as well as of an example specifically describing the conditions of implementation of the hydrolysis stage of butyl hydrogen sulphate (Example 4).

In these examples, all the percentages are expressed by weight, except when otherwise indicated; BUA denotes butyl acrylate and BUHS denotes butyl hydrogen sulphate ($BuSO_4H$). The ratios indicated in the examples are ratios by weight.

EXAMPLE 1

360 g of acrylic acid, 481 g of butanol, 64 g of BUA and 13 g of sulphuric acid are reacted, for a period of 2 hours 10, at a temperature of 80°–100° C., in a reactor with a capacity of 1 litre. The water generated (92 g) is distilled off in the column surmounting the reactor as it is formed, in the form of an azeotropic mixture with butanol and BUA, which mixture is separated in a decanter into an organic phase, recycled at the head of the column, and an aqueous phase, which is drawn off. On conclusion of the reaction stage, the medium is composed of 642 g of BUA, 113 g of butanol, 18 g of acrylic acid and 20 g of catalyst in the form of BUHS.

55 g of the aqueous phase recovered during the reaction are added to this crude mixture and hydrolysis of BUMS to sulphuric acid and butanol is carried out, in a non-continuous mode at 80° C., for 30 minutes. On conclusion of this stage, the mixture is separated into an aqueous phase (72 g), containing sulphuric acid (12.1 g) as well as 0.6 g of unconverted butyl sulphate and 3.6 g of acrylic acid, and an organic phase (804 g), containing 0.5 g of butyl sulphate and 14.4 g of acrylic acid. The hydrolysis yield is 95%.

The organic phase is neutralized with 107 g of a 2 N aqueous sodium hydroxide solution, i.e. a 5% excess with respect to the sum of the acidities present. After separation by settling, the organic phase is non-acidic. It is washed with a mixture composed of the remainder of the aqueous phase recovered during the reaction, i.e. 37 g, to which 100 g of fresh water are added.

The alkaline aqueous phase (121 g), obtained after neutralization with sodium hydroxide, is reacidified in order to regenerate acrylic acid by adding to it a mixture composed of the acidic aqueous phase (72 g) obtained after hydrolysis of BUHS. Under these conditions, the excess acidity with respect to stoichiometry necessary to displace the acids (acrylic acid, traces of butyl sulphate) from their salts is 17%. It is consequently unnecessary to add fresh sulphuric acid. After stirring for 5 minutes, an aqueous solution (192 g) is obtained which contains 17.8 g of acrylic acid, 1 g of butyl hydrogen sulphate and 1.8 g of sulphuric acid, as well as 15 g of sodium sulphate.

Extraction of the acrylic acid and the BUHS with a mixture composed of 481 g of butanol and 64 g of BUA is then carried out, this mixture representing the combination of the flows of alcohol and ester introduced at the esterification stage (fresh butanol and butanol and BUA mixture recovered in the column for removal of the light products). Under these conditions, the extraction ratio of the organic phase to the aqueous phase is 2.8.

An organic phase is recovered which contains 17 g of acrylic acid and 0.7 g of BUHS and an aqueous phase is recovered which contains 1 g of acrylic acid, 0.3 g of BUHS and 1.8 g of free sulphuric acid, as well as all the sodium sulphate present beforehand in the acidic aqueous phase. The extraction yields of acrylic acid and BUHS are 94% and 70%, respectively.

The acidity present in the aqueous phase resulting from the extraction stage is neutralized by adding 27 g of 2 N sodium hydroxide. This stage generates 4 g of salt in the form of sodium sulphate.

It is calculated, per 1000 g of BUA obtained on conclusion of the esterification reaction, that the discharges of organic pollution to water, directly related to the presence of acrylic acid and butyl sulphate, represent an overall COD of 2.6 g $O_2$ and that the saline discharges represent 30 g in the form of sodium sulphate.

EXAMPLE 2 (Comparative example)

On conclusion of an esterification reaction carried out under conditions identical to Example 1, a reaction medium is obtained which contains 638 g of BUA, 116 g of butanol, 20 g of acrylic acid and 19 g of BUHS.

The operation is carried out in the same way as that described in Example 1, save for the fact that the BUHS present is not hydrolysed.

After the neutralization stage, carried out by addition of 210 g of 2 N sodium hydroxide, all the acrylic acid and BUHS are present in the aqueous phase, in the sodium salt form.

This aqueous solution is reacidified with 23.7 g of sulphuric acid, so as to regenerate all the acrylic acid and BUHS from their sodium salts, a 15% excess of acid being used with respect to stoichiometry.

The acrylic acid and BUHS in this aqueous solution (248 g) are extracted with the same amounts of butanol (481 g) and BUA (64 g) as those used in Example 1. The extraction ratio of organic solvent to the aqueous phase is 2.2.

After extraction, an organic phase is recovered which contains 18.5 g of acrylic acid and 12.4 g of BUHS and an aqueous phase is recovered which contains 1 g of acrylic acid. 6.5 g of BUHS and 2.9 g of sulphuric acid.

The aqueous phase thus obtained is neutralized with 60 g of 2 N sodium hydroxide (5% excess). This neutralization stage generates 11 g of salt in the sodium sulphate form.

It is calculated, per 1000 g of BUA obtained on conclusion of the esterification reaction, that the discharges of organic pollution to water, directly related to the presence of acrylic acid and of butyl sulphate, represent an overall COD of 14.8 g $O_2$, i.e. 5.7 times more than in Example 1, and that the saline discharges represent 65 g in the sodium sulphate form, i.e. 2.1 times more than under the conditions of Example 1.

EXAMPLE 3

A mixture composed of acrylic acid and butanol in an alcohol/acid molar ratio of 1.3/1, 7% BUA (in order to simulate recycling of the light products recovered at the head of the topping column) and 1.1% of 95% sulphuric acid is reacted at reduced pressure, for a period of 2h20, at a temperature of 80°–100° C., in a stirred reactor surmounted by a distillation column equipped with a decanter at the head and heated using an electrical reactor heater. The water generated by the reaction is distilled off, as it is formed, in the column surmounting the reactor, in the form of an azeotropic mixture with butanol and BUA, which mixture is separated in the decanter into an organic phase, recycled at the head of the column, and an aqueous phase, which is drawn off. On conclusion of the reaction stage, the medium is composed of BUA (82%), butanol (13%), acrylic acid (2.25%) and catalyst in the form of BUHS (1.8%).

The crude product thus obtained is conveyed continuously (1265 g/h), at the same time as a part of the aqueous phase recovered in the decanter during the esterification (95 g/h), into a reactor composed of a Teflon pipe with a diameter of 6 mm and a length of 3.2 m which is filled with carborundum (silicon carbide) beads in order to provide for contact of the reactants. The reactor is immersed in an oil bath maintained at 130° C. at a pressure of 2 bars. The residence time of the reaction mixture is 2 minutes. On conclusion of this stage, the mixture is separated into an aqueous phase (91 g/h) containing 17.2% of regenerated sulphuric acid and an organic phase (1277 g/h) containing 0.03% of butyl sulphate and 2.6% of acrylic acid; the hydrolysis yield of BUHS is 98.4% and the hydrolysis yield of BUA is limited to 0.3%.

The organic phase is neutralized with a 2 N aqueous sodiumhydroxide solution, with a 10% excess with respect to the sum of the acidities present. After separation by settling, the organic phase is non-acidic.

The alkaline aqueous phase obtained after neutralization with sodium hydroxide (i.e. 1 part) is mixed with the acidic aqueous phase obtained after hydrolysis of BUHS (i.e. 0.25 part) and 95% sulphuric acid (i.e. 0.17 part) is added to this mixture. Under these conditions, the excess acidity with respect to stoichiometry necessary to displace the acids (acrylic acid, traces of butyl sulphate) from their salts is 10%. After stirring for 5 min, an aqueous solution is obtained which contains 10.2% of acrylic acid.

The acrylic acid is then extracted with a mixture representative of the composition of the flow obtained at the head of the column for washing with water (9/1 BUA/butanol mixture), in an extraction ratio of the organic phase to the aqueous phase of 0.6/1. The extraction is carried out continuously in a unit containing 4 mixers/decanters in series, each representing a true extraction stage, where the aqueous and organic phases meet in a countercurrent mode. This system faithfully represents a conventional extraction column containing 4 theoretical stages.

An organic phase containing 12% of acrylic acid, 3.8% of water and only 13 ppm of salts expressed as sodium sulphate, on the one hand, and an aqueous phase containing less than 0.1% of acrylic acid, as well as all the salts initially present in the acidic aqueous phase, on the other hand, are recovered at the outlet of the extraction unit. The extraction yield of acrylic acid in the solvent is 98%. The content of salts in the extracted organic phase (13 ppm) is compatible with recycling this phase to the reaction stage without washing. In fact, it could be determined that the solubility of sodium sulphate in the dehydrated reaction medium of the esterification reaction is 120 ppm; there is therefore no salting out of salts during esterification. However, washing with water in order to remove the last traces of salts has been tested.

According to a variant of the extraction conditions described above, this extraction is carried out over three stages and washing the extracted organic phase with water is carried out over the 4th stage. The same aqueous and organic flows are conveyed in countercurrent mode over the first three stages of the unit, and the organic phase exiting from the 3rd stage is conveyed to the 4th stage, in which pure water is introduced in countercurrent mode. The flows supplying the unit are in an acidified aqueous phase/solvent/pure water ratio of 1/0.6/0.1. In this case, the extraction yield of acrylic acid in the extracted organic phase is 94% and the content of salts, expressed as sodium sulphate, is 0.5 ppm.

According to a second variant of the extraction conditions, this extraction is carried out over the 4 stages of the unit containing mixers/decanters, by conveying, in countercurrent mode, the aqueous phase to be extracted, on the one hand, and pure BUA, on the other hand, in a solvent/aqueous phase ratio of 0.6/1. The extraction yield of sulphuric acid is 93%, the concentration of water in the extracted organic phase is 2.9% and that of the salts is less than 0.2 ppm.

The saline discharges, recovered fully in the stripped water, represent, from calculation, 40 g per 1000 g of purified BUA.

EXAMPLE 4

In this example, the conditions of hydrolysis of BUHS in a crude reaction mixture from the synthesis of BUA are varied in a continuous mode and the hydrolysis yields of BUHS (desired reaction) and of BUA (undesirable side reaction) are measured.

The crude mixture obtained at the end of the esterification reaction of acrylic acid by butanol is composed of 83% BUA, 10.5% butanol, 0.2% acrylic acid and 1.7% BUHS.

The reaction is carried out in various types of reactors fed in a continuous mode:

- stirred reactor with a capacity of 0.5 litre, heated by an external double jacket containing circulating oil
- tubular reactor with a diameter of 6 mm, optionally filled with carborundum (silicon carbide) beads
- tubular reactor with a diameter of 1.5 mm which is not filled.

The results of the various tests are summarized in the Table below, in which Y1 denotes the hydrolysis yield of BUHS and Y2 denotes the hydrolysis yield of BUA.

| Type of reactor | | | | | | | Filled tube | | Empty tube | |
| --- | --- | --- | --- | --- | --- | --- | --- | --- | --- | --- |
| Tube diameter | | Stirred reactor | | | | | 6 mm | | 6 mm | 1.5 mm |
| Temperature (°C.) | 60 | | 80 | | 95 | 105 | 115 | 130 | 130 | 145 |
| Absolute pressure (bars) | 1 | 1 | 1 | 1 | 1 | 1 | 1.5 | 2 | 2 | 2.6 |

| Type of reactor | Stirred reactor | | | | | | Filled tube | | | Empty tube | |
|---|---|---|---|---|---|---|---|---|---|---|---|
| Tube diameter | | | | | | | 6 mm | | | 6 mm | 1.5 mm |
| H$_2$O/crude mixture | 7 | 7 | 14 | 7 | 7 | 7 | 7 | 7 | 3 | 7 | 7 |
| Residence time (min) | 30 | 30 | 30 | 60 | 15 | 20 | 2 | 1 | 1 | 2 | 20 sec |
| Yield Y1 (%) | 15 | 86 | 85 | 89.5 | 90 | 98.5 | 98.4 | 98.5 | 86 | 97.1 | 95.7 |
| Yield Y2 (%) | 0.4 | 0.8 | 0.9 | 1.9 | 0.8 | 1 | 0.3 | 0.4 | 1.3 | 0.8 | 0.3 |

We claim:

1. Process for the manufacture of butyl acrylate by direct esterification of acrylic acid by butanol, the said esterification being catalysed by sulphuric acid, the water of reaction being removed, during all or part of the reaction, in the form of an azeotropic mixture with butanol and butyl acrylate, the crude reaction mixture obtained comprising butyl acrylate, butanol, acrylic acid, butyl hydrogen sulphate and traces of sulphuric acid, characterized in that:

(a) butyl hydrogen sulphate is hydrolysed (in R2) to sulphuric acid using pure water (18) or using water (2) generated during the reaction;

(b) the medium, after hydrolysis, is separated by settling (in D2) into:
   an organic phase containing butyl acrylate, butanol and a part of the unconverted acrylic acid; and
   an aqueous phase containing sulphuric acid and the remainder of the unconverted acrylic acid;

(c) the organic phase is washed under alkaline conditions for the purpose of neutralizing the acrylic acid to alkaline acrylate which is soluble in the aqueous phase and the neutralized organic phase is then washed with water;

(d) the acrylic acid present in the alkaline salt form in the aqueous phase of the first basic neutralization is regenerated by addition of the acidic aqueous phase (8) resulting from the separation by settling (in D2) of the hydrolysis stage and, optionally, of a complement of sulphuric acid (9);

(e) the acrylic acid (10) thus regenerated in this aqueous phase is extracted (in C5) by a solvent chosen from butanol, butyl acrylate or a mixture of butyl acrylate and butanol;

(f) the organic phase (13) obtained at the head of the extraction column (C5), containing acrylic acid and butanol or butyl acrylate or a mixture of butanol and butyl acrylate, is recycled in the esterification reactor (R1);

(g) the aqueous phase (15), recovered at the foot of the solvent extraction column (C5), is conveyed, optionally after neutralization with sodium hydroxide (in 14), as feed to a distillation column (C6) which makes it possible to recover butanol (16) at the head, for the purpose of recycling it upstream in the process, and to discard the spent aqueous liquors, which are virtually free from organic pollution.

2. Process according to claim 1, characterized in that the hydrolysis in stage (a) is carried out in a stirred reactor or a plug flow reactor (R2), to which is sent the crude reaction mixture obtained after the end of the esterification reaction, at a temperature of 50° to 200° C., and at a pressure which is sufficient to prevent boiling of the medium, by adding pure water (18) and/or water (2) generated by the esterification reaction, in a proportion of 3 to 50% by weight with respect to the crude reaction mixture, for a time from 10 seconds to 2 hours.

3. Process according to claim 2, characterized in that the hydrolysis is carried out at a temperature of 70° to 150° C., by adding pure water (18) and/or water (2) generated by the esterification reaction in a proportion of 4 to 20% by weight with respect to the crude reaction mixture, for a time of 10 seconds to 1 hour.

4. Process according to claim 1 characterized in that the two washing operations of stage (c) are carried out in a washing column (C2) supplied:
at the bottom, with the organic phase (3) resulting from the hydrolysis stage;
in the middle of the column, with an aqueous sodium hydroxide solution;
at the head of the column, with fresh water or the remainder of the water of reaction (4) mused in the hydrolysis stage.

5. Process according to claim 1, characterized in that the two washing operations of stage (c) are carried out by neutralizing the organic phase (3) resulting from the decanter (D2) with a basic solution and by sending the resulting neutralized phase to a new decanter (D3), the organic phase (19) resulting from the said decanter (D3) being conveyed to the foot of a washing column (C2) supplied at the head with pure water (20) and/or a portion (4) of the water generated in the esterification reaction, the phase (22) drawn off from the foot of the said washing column (C2) being sent to the distillation column (C6).

6. Process according to claim 1, characterized in that the extraction stage (e) is carried out in an extraction column (C5) supplied at the head with the acidified aqueous phase (10), and, at the foot, with the solvent (11; 12).

7. Process according to claim 1, characterized in that the solvent of stage (e) comprises all or part of the butanol (11) necessary for the esterification reaction, optionally completed by all or part of a mixture (12) mainly comprising butyl acrylate and butanol, resulting from columns for topping the washed crude reaction mixture and the aqueous effluents of the process.

8. Process according to claim 1, characterized in that the solvent (12) of stage (e) comprises pure butyl acrylate with, if appropriate, butanol, the butyl acrylate/butanol ratio by weight being in particular between 1/0 and 1/0.5.

9. Process according to claim 8, characterized in that the solvent is composed of all or part of the washed crude reaction mixture (5) or is composed of a mixture of pure butyl acrylate and all or part of the flows (16) and/or (17) obtained at the head of the columns for topping the washed crude reaction mixture and the aqueous effluents of the process.

10. Process according to claim 1, characterized in that it is carried out continuously.

11. Process according to claim 1, characterized in that it is carried out non-continuously.

* * * * *